United States Patent
Yang (10) Patent No.: US 10,405,791 B2
(45) Date of Patent: Sep. 10, 2019

(54) METHOD AND CONTINUOUSLY WEARABLE NONINVASIVE APPARATUS FOR AUTOMATICALLY DETECTING A STROKE AND OTHER ABNORMAL HEALTH CONDITIONS

(71) Applicant: Yingchang Yang, Palo Alto, CA (US)

(72) Inventor: Yingchang Yang, Palo Alto, CA (US)

(73) Assignee: Yingchang Yang, Palo Alto, CA (US)

( * ) Notice: Subject to any disclaimer, the term of this patent is extended or adjusted under 35 U.S.C. 154(b) by 337 days.

(21) Appl. No.: 13/831,897

(22) Filed: Mar. 15, 2013

(65) Prior Publication Data

US 2014/0276123 A1 Sep. 18, 2014

(51) Int. Cl.
*A61B 5/00* (2006.01)
*A61B 5/021* (2006.01)
*G16H 40/63* (2018.01)
*G16H 50/20* (2018.01)
*A61B 5/024* (2006.01)

(52) U.S. Cl.
CPC ........ *A61B 5/4076* (2013.01); *A61B 5/02125* (2013.01); *A61B 5/6801* (2013.01); *A61B 5/7275* (2013.01); *G16H 40/63* (2018.01); *G16H 50/20* (2018.01); *A61B 5/02416* (2013.01); *A61B 2562/0219* (2013.01)

(58) Field of Classification Search
CPC .......................... A61B 5/4076; A61B 5/02125
See application file for complete search history.

(56) References Cited

U.S. PATENT DOCUMENTS

| 2005/0096557 A1* | 5/2005 | Vosburgh | A61B 5/02125 600/509 |
| 2008/0161707 A1* | 7/2008 | Farringdon et al. | 600/509 |
| 2011/0054277 A1* | 3/2011 | Pinter | A61B 5/0205 600/310 |

* cited by examiner

*Primary Examiner* — Christian Jang
(74) *Attorney, Agent, or Firm* — Bo-In Lin (57) ABSTRACT

Method and continuously wearable noninvasive apparatus for automatically detecting a stroke's onset are invented. The method comprises measuring pulse transit time or a related hemodynamic parameter and using adaptive pattern learning and stroke identification algorithms to identify the start of a stroke attack. The algorithms are run on an embedded processor and electronics in the apparatus. The result of the identification and detection is used to generate an alarm to alert the patient, caregiver or medical professional to immediately seek further medical treatment. The method can also be applied to identify and detect other abnormal health conditions.

13 Claims, 10 Drawing Sheets

METHOD AND CONTINUOUSLY WEARABLE NONINVASIVE APPARATUS FOR AUTOMATICALLY DETECTING A STROKE AND OTHER ABNORMAL HEALTH CONDITIONS

This patent application is a non-provisional application and claims the priority date of a Provisional Application 61/640,651 filed on Apr. 30, 2012 by a common inventor of this application. The disclosures made in the Patent Application 61/640,651 are hereby incorporated by reference in this patent application.

FIELD OF INVENTION

The present invention relates generally to devices and methods for measuring and monitoring a person's physical conditions. More particularly, this invention relates to non-invasive methods and continuously wearable apparatus for automatically monitoring and detecting a person's stroke onset and other abnormal health conditions.

BACKGROUND OF THE INVENTION

A stroke is a brain disease either by ischemia caused by a cerebral artery blockage or by hemorrhage when a blood vessel ruptures and bleeds into the brain. According to American Stroke Association (www.strokeassociation.org), strokes are currently the $4^{th}$ cause of death and a $1^{st}$ reason of disability in the United States. About 780,000 strokes occur annually in the US. Strokes have incurred tremendous impact and financial cost to our society. Projected cost is estimated to be about 2.2 trillion dollars by 2050 (Brown, et al., "Projected costs of ischemic stroke in the United States", Neurology, 67(8):1390-1395 (2006)). It is imperative to have a more effective method to improve the treatment and prevention of the disease.

Early Alert is Critical for Stroke Treatment:

The key for effective stroke care is time from its onset to receiving medical treatment. The first line standard medicine against an ischemic stroke, which represents about 87% of all strokes, is a thrombolytic drug called tissue plasminogen activator (tPA) (Adams, et al., "Guidelines for the early management of adults with ischemic stroke", Stroke, 38:1655-1711 (2007)). The tPA was approved by the FDA in 1996. It can dissolve the blood clot and restore the blood flow. The thrombolytic therapy can significantly reduce or reverse the effects of a stroke and prevent permanent disability. However, the tPA needs to be given to an ischemic stroke patient within 3 hours after the stroke's onset. After the 3 hour window, the drug is no longer effective and may increase the risk of bleeding inside the brain. In order to keep explanation concise, the description in this patent application focuses more on the ischemic stroke while the present invention can be applied to both ischemic and hemorrhagic strokes.

Hemorrhagic stroke, which stands for about 13% of all strokes, has a high mortality rate of ~40%. While no medicine for the hemorrhagic stroke has the 3 hour limit, it still requires prompt treatment. Usually half of the deaths happen within the first 2 days (Joseph, et al., "Guidelines for the management of spontaneous intracerebral hemorrhage", Stroke. 30:905-915 (1999)), (Bederson et al., "Guidelines for the management of aneurysmal subarachnoid hemorrhage", Stroke, 40: 994-1025 (2009)). The disease is considered one of the highest degree medical emergencies. Early diagnosis and treatment are needed to reduce the mortality.

Unfortunately, "Generally, only 3 to 5 percent of those who suffer a stroke reach the hospital in time to be considered for this treatment" according to American Stroke Association (www.strokeassociation.org). About 95% of the ischemic stroke patients missed the thrombolytic therapy, which is the treatment of choice. Unlike heart attack symptoms which usually include severe chest pain, stroke symptoms vary much depending on where a stroke occurs in the brain. Severe strokes can have sudden numbness, vision change, imbalance, trouble in speaking or walking, headache etc. In other cases, the initial symptoms may be mild depending on which blood vessel inside the brain is blocked. The symptoms may be mistakenly considered as causes of other health conditions such as aging or sickness. Sometimes, a stroke patient may not be aware of any abnormality during sleep until wake-up. Many strokes are painless. All of these factors lead to a delay by a stroke patient to seek immediate medical diagnosis and the critical thrombolytic therapy. Early detection and alarm of a stroke's onset are pivotal for improving current stroke management.

Current standard technologies for stroke diagnosis are Computed Tomography (CT), Magnetic Resonance Imaging (MRI) and Ultrasound. These detections are accurate. However, they are expensive equipment. The procedures can only be done by a medical professional in a hospital or clinic. CT and MRI need specially shielded room. A potential stroke patient cannot be put under the continuous monitoring by the equipments. The three technologies are good for stroke diagnosis in hospital, but not appropriate for regular daily use at home or office for an early stroke alarm to help bring a stroke patient to a hospital for early medical treatment.

Therefore it is highly desirable to have an alarm device to automatically detect and promptly alert the onset of a stroke attack. The device needs to be continuously wearable because the time when a stroke starts is unknown. A potential stroke patient needs to be continuously monitored. The device shall have good accuracy and coverage of different stroke types. It is also desirable to be non-invasive and simple to operate. The alarm can be sent as an alert to the patient, a caregiver or medical professional to immediately seek further medical diagnosis by CT, MRI or ultrasound and treatment like tPA.

The stroke alerts, as that practiced by those of ordinary skill in the art, are not adequate and not able to effectively help fight against a stroke or save a life.

Several patented disclosures have tried to detect a stroke's onset by asking the patient to perform certain physical tasks related to stroke symptoms. For example, U.S. Pat. No. 2007/0021687 A1 instructed a patient to do strength measurements to make detection. U.S. Pat. No. 6,592,378 B2 asked the patient to answer several symptoms-related questions to decide whether a stroke has occurred. U.S. Pat. No. 2008/0294019 A1 uses chest movement, patient position and other vital signs as criteria for a stroke alert. All these methods are based on external physical symptoms of a stroke. However, they can only cover certain cases with obvious symptoms. The detections often lag well behind the start of a stroke attack. These methods may not work if a stroke happens during sleep. Most of the methods are not automatic and need a patient's involvement. These methods will lead to a delay for stroke treatment.

Another technique is based on monitoring the changes of a biochemical component or marker in the blood or other biological samples. For example, US 2010/0167322 A1 measures the aldehyde compounds. U.S. Pat. No. 7,427,490, B2 detects the presence of a certain chemical marker such as a B-type natriuretic peptide from a patient's blood sample. The technique is invasive and needs to take biological samples from a patient. These reasons make the technique inconvenient or improper for continuous monitoring.

Other known prior art includes electroencephalogram (EEG), brain wave, and impedance plethysmography (IPG) or photoplethysmography (PPG) on a patient's head such as US 2011/0245707 A1 and US 2011/0201950 A1. EEG and brain wave use multiple electrical nodes attached the head to detect the electrical functional activity of the brain. The methods are more sensitive for seizure, which involves high abnormity of electrical signaling in the brain. A stroke can be due to any big or small blood vessel. The effect on cerebral electrical signaling by a stroke may or may not be significant. As a result, EEG and brain wave may only cover a small percentage of stroke cases. IPG measures cerebral impedance change. PPG on head measures volumetric change of cerebral blood. Similar to the EEG, the IPG/PPG methods are sensitive to certain severe cerebral changes such as big vessel blockage and insensitive to deep or small vessel damages. As of now, no coverage information based on a large number of clinical stroke cases has been reported for these methods. Overall, these methods may have limited coverage of stroke cases. In addition, wearing a bulky device on head may not appeal to patients.

Because of the limits as described above, none of the prior arts has successfully brought a viable stroke alarm product to stroke patients so far. Potential stroke patients still live in constant fear of a possible stroke attack and worry about when a stroke will come and how to prepare for the attack.

Thus a new method and device are needed to alarm a stroke's onset. The device shall be continuously wearable, non-invasive, simple to operate and with good accuracy and coverage of different stroke types. The invention of the current patent presents such a device to a stroke patient. The present patent is based on extensive research and analysis on the clinical evidences and data about stroke and blood pressure as summarized in Paragraph [0015-0018].

It has been known for years that the blood pressure (BP) spontaneously changes in most stroke patients (Wallace, et al., "Blood pressure after stroke", JAMA 246(19): 2177-2180 (1981)). In a study involved in 563,704 stroke patients presenting to the emergency departments, 69% showed elevated blood pressure at the time of admission (Qureshi, et al., "Prevalence of Elevated Blood Pressure in 563,704 Adult Patients Presenting to the Emergency Department with Stroke in the United States", Am J Emerg Med, 25(1): 32-38 (2007)). In another study by the International Stroke Trial from 467 hospitals in 36 countries, ~82% of 17,398 patients had high blood pressure based on the WHO definition of hypertension (systolic BP>140 mm Hg) within the first 48 hours following acute stroke (Leonardi-Bee, et al., "Blood pressure and clinical outcomes in the International Stroke Trial", Stroke. 33: 1315-1320 (2002)). Some of the stroke patients did not have prior history of hypertension. Some of the patients had hypertension before (Rodriguez-Yanez, et al., "New-onset hypertension and inflammatory response/poor outcome in acute ischemic stroke", Neurology, vol. 67, no. 11: 1973-1978 (2006)). Other research studied the prognostic significance of the initial blood pressure change (Aslanyan, et al. "Effect of blood pressure during the acute period of ischemic stroke on stroke outcome: a tertiary analysis of the GAIN International Trial", Stroke, 34(10): 2420-2425 (2003)); (Rodriguez-Garcia J L, et al. "Significance of elevated blood pressure and its management on the short-term outcome of patients with acute ischemic stroke", Am J Hypertens 18(3):379-384 (2005)). The BP pattern change is believed to be a natural compensatory auto-regulation mechanism to maintain cerebral blood flow and reduce neuronal death while the presence of the ultra high blood pressure for an extended time may incur damage as well (Yong, et al., "Characteristics of blood pressure profiles as predictors of long-term outcome after acute ischemic stroke", Stroke, 36:2619-2625 (2005)).

On the other hand, BP is also known for its intrinsic fluctuation and instability for decades since a BP measurement technique became available. BP is not constant even for a normal healthy person. When BP is measured at different times for the same person, the measured BP values may be different. BP may go up and down multiple times within a day (Millar Craig, et al., "Circadian Variation of Blood-Pressure", The Lancet, April 15: 795-797 (1978)). BP is also affected by the person's mood, motion, food, drug etc (Räikkönen, et al., "Effects of hostility on ambulatory blood pressure and mood during daily living in healthy adults", Health Psychology, Vol 18(1), 44-53 (1999)) (James, et al., "The influence of happiness, anger and anxiety on the blood pressure of borderline hypertensives", Psychosomatic Medicine Vol. 48, No. 7 (1986)). BP is believed to be continuously changing naturally. The general perception of the normal BP variations and lack of a continuous BP measurement technology may have prevented proposing use of BP change for stroke detection.

The present patent did a further research and analysis about the detail characteristics of BP and finds that the BP pattern after a stroke's onset is different from that of normal BP fluctuations as described in Paragraph [0016]. The BP after a stroke's onset showed different dynamic and pattern. The BP change in a stroke event is usually within about half hour and takes about hours to days to fall back to the pre-stroke level (Broderick, et al., "Blood pressure during the first minutes of focal cerebral ischemia", Ann Emerg Med., 22(9):1438-43 (1993)), (Ntaios, et al., "Blood pressure change and outcome in acute ischemic stroke: the impact of baseline values, previous hypertensive disease and previous antihypertensive treatment", Journal of Hypertension, Vol 29 (8): 1583-1589 (2011)), (Semplicini, et al., "Hypertension in acute ischemic stroke: A compensatory mechanism or an additional damaging factor?", Arch Intern Med, vol 167: 211-216 (2003)). However, the normal BP changes but stays around the baseline (Gardner, et al., "24-Hour Ambulatory Blood Pressure Monitoring in Primary Care", JABFP, Vol 14, No 3: 166-171 (2001)). If the patient does not have history of hypertension, the BP will normally stay below the hypertension zone, <140 mmHg for systolic BP. If the patient has prior hypertension, the BP will stay around the patient's base level (Khoury, et al., "Ambulatory blood pressure monitoring in a nonacademic setting. Effects of age and sex", Am J Hypertension, 5(9):616-23 (1992)). When there is a change, the change tends to be short and quickly returns to the base curve and trend.

After studying a large amount of clinical data and evidences about BP and stroke as summarized above, the present patent concludes that the BP pattern after a stroke's onset is distinguishable from the patient's normal BP fluctuation pattern. The current patent further proposes to continuously monitor BP or a BP-related hemodynamic parameter for detecting a stroke's onset. However, currently there is no effective method and apparatus in the field of medical device industries to continuously monitor the blood pressure and set a stroke alarm that can be carried out conveniently and comfortably for a long time. A stroke occurs unexpectedly. The monitoring device needs to be continuously wearable for days, weeks, years or even a patient's whole life.

Current BP measurement technologies do not fit the requirements for noninvasive continuous wearing for detecting a stroke's onset. They are for a short term test, not for a long term use. The BP measurement methods on market include invasive vascular pressure monitoring, sphygmomanometer and oscillometry. The invasive vascular pressure method involves placing a cannula needle or catheter into an artery. This method is most accurate. However, apparently it is not proper for continuous everyday wearing. Sphygmomanometer uses a stethoscope and a cuff to do the measurement based on Korotkoff sounds. Oscillometry uses a cuff and electronics to decide the blood pressure based on cuff pressure oscillations. Both sphygmomanometer and oscillometry need to inflate and deflate the burdensome cuff, which interrupts regular sleep and activities. The methods can measure blood pressure but they are cumbersome and uncomfortable. They cannot be used for continuous ambulatory BP measurement for a long time. A patient cannot wear them on a regular daily bases. So these BP measurement technologies are not suitable for use for a stroke alert, which requires monitoring the BP change continuously.

For these reasons, in addition to using BP as the basis for stroke detection and alert, it is also required to have a new technical approach. In order to overcome the above difficulties and problems, the apparatus must be continuously wearable, uses no cuff and does not require complex procedures to operate. The invention in the current patent presents such a new method and apparatus for a stroke onset alarm by further proposing to utilize and analyze another hemodynamic parameter, pulse transit time (PTT). The pulse transit time is the time for an arterial pulse wave to propagate between two different arterial sites. PTT is another characteristic parameter of blood circulation and related to BP (Paragraph [0047]). The above clinical observation (Paragraph [0015-0018]) about the relationship between a stroke's onset and BP change can be extrapolated to the relationship between the stroke's onset and PTT change. More importantly, unlike the BP measurement technologies, the method and apparatus in the present patent for monitoring and analyzing PTT to identify and detect a stroke's onset fit the requirements for long term use for a stroke alert such that the aforementioned difficulties and problems can be overcome.

SUMMARY OF THE INVENTION

It is an aspect of the present invention to provide an apparatus to implement an entirely new monitoring system with improved methods for detecting a stroke's onset. The apparatus is non-invasive, continuously wearable and simple to operate and With good accuracy and coverage of different stroke types. A stroke alert is automatically generated to achieve the purpose of timely providing medical treatment to the patient within the limited time window such that the patient's life can be saved or the damage caused by a stroke can be cured or minimized.

In an embodiment of the invention, a method is provided for monitoring a potential stroke patient to detect a stroke's onset, comprising steps of:

1). Continuously wearing two separate pulse wave sensor units on two different arterial sites on a patient's body. During each cardiac cycle, the heart generates a pulse wave that travels along the arteries. The pulse wave is also called pressure wave, pressure pulse wave, pulse pressure wave, etc. An arterial site is a region of skin above at least one arterial vessel on a human body. The pulse wave sensor can measure the pulse wave directly or indirectly by measuring the physical or physiological changes caused by the pulse wave at an arterial site.

2). Sampling and recording the pulse waveform from each sensor unit;

3). Calculating the time difference, pulse transit time (PTT), between the two waveforms;

4). Processing the PTT, adaptively learning the normal PTT pattern, making an alarm indication when an anomalous PTT pattern is detected and identified to be corresponding to the PTT pattern of a stroke's onset.

5). Indicating the time when the PTT change starts. The time indication is important for prescribing a thrombolytic drug like tPA.

In another embodiment of the invention, electronics, hardware and software are described to implement the method. The procedures after wearing are completed automatically by electronics and software. Digital sampling is done by an analog to digital converter (ADC). The sampling result is recorded into an electronic memory. The calculation and processing are executed by a processor and software. The alert includes an audio alarm and an alert to a remote agent via a wireless or wired technology or both. The patient's location measured by a global positioning system (GPS) is also included in the alert message. A motion sensor is used to measure the patient's movement. A user interface is provided to program the device and show the result. A power supply is used in the apparatus to provide power for continuously wearing and monitoring.

Therefore, the present invention provides a method to continuously monitor the PTT of a person who wears the device to noninvasively monitor and detect a stroke's onset. Embodiments of the present invention provide a new medical device for detecting a stroke's onset, which includes following special features:

1) Noninvasive. A potential stroke patient wears the device on the surface of his or her body. No requirement for drawing blood or other biological sample is needed. It is painless. No chemical test is involved.

2) Wearable. The apparatus is small and inexpensive. Unlike bulky CT, MRI or ultrasound equipment, it can be easily worn on human body.

3) Continuously. It is light and comfortable to wear for a long time like a watch. The sensor unit uses a different mechanism to detect the arterial pulse wave. No cuff is used. The patient can still perform regular activities and sleep at home, office or on travel.

4) Appealing. The device is worn on body such as arm or leg etc. It is not noticeable by other people unlike those devices on head. So a patient is more willing to comply to wear it.

5) Coverage. The method is based on natural auto regulation by human body when a stroke occurs. It has a good coverage of different stroke types involving big or small, deep or shallow blood vessels with good accuracy for detecting a stroke's onset.

6) Automatic. The monitoring and detection are automatically done by the apparatus and its software. An alarm is immediately generated to the patient, caregiver or medical personnel when a stroke's onset is detected.

It is a further aspect that the method of the present invention is based on natural auto regulation response to a stroke attack by human body. This improved method is based on the research on enormous amount of clinical data that has shown the prevalence of sudden pattern change of a blood circulation characteristic, blood pressure, in patients after a stroke attack (Paragraph [0015-0018]). Specifically, the present invention provides methods and apparatus to detect the changes of a BP-related hemodynamic parameter PTT during normal time and when a stroke occurs and further sends out alarm to timely and effectively treat a patient in an early stage of a stroke's onset. The present invention thus overcomes the limits and ineffectiveness of current BP measurement technologies by continuously monitoring PTT using a practical and convenient wearable apparatus and improved detection methods to carry out the tasks on a regular daily basis.

In another embodiment, in addition to detect a stroke's onset, the method and apparatus disclosed in the patent is also used to monitor, identify and detect other related abnormal health conditions such as hypertension, hypotension, arrhythmia, myocardial infarction, vascular aneurysm, congestive heart failure, valvular heart disease, cardiac muscle disease, death or another disease causing a characteristic pattern change of PTT or a PTT-related hemodynamic parameter.

The apparatuses and methods are illustrated in the drawings. The following descriptions of each figure give more explanations about the apparatus and method of this invention. Note that the figures are for the purpose of illustration. Actual physical implementation may take a variety of different forms. All changes and substitutions within the spirit and technical scope of the invention are indeed encompassed in the present patent. These and other objects and advantages of the present invention will no doubt become obvious to those of ordinary skill in the art after having read the following detailed description of the embodiments.

BRIEF DESCRIPTION OF THE DRAWINGS

The present invention is herein accompanied with illustrative drawings.

DETAILED DESCRIPTION OF EMBODIMENTS OF THIS INVENTION

Figure 1A:
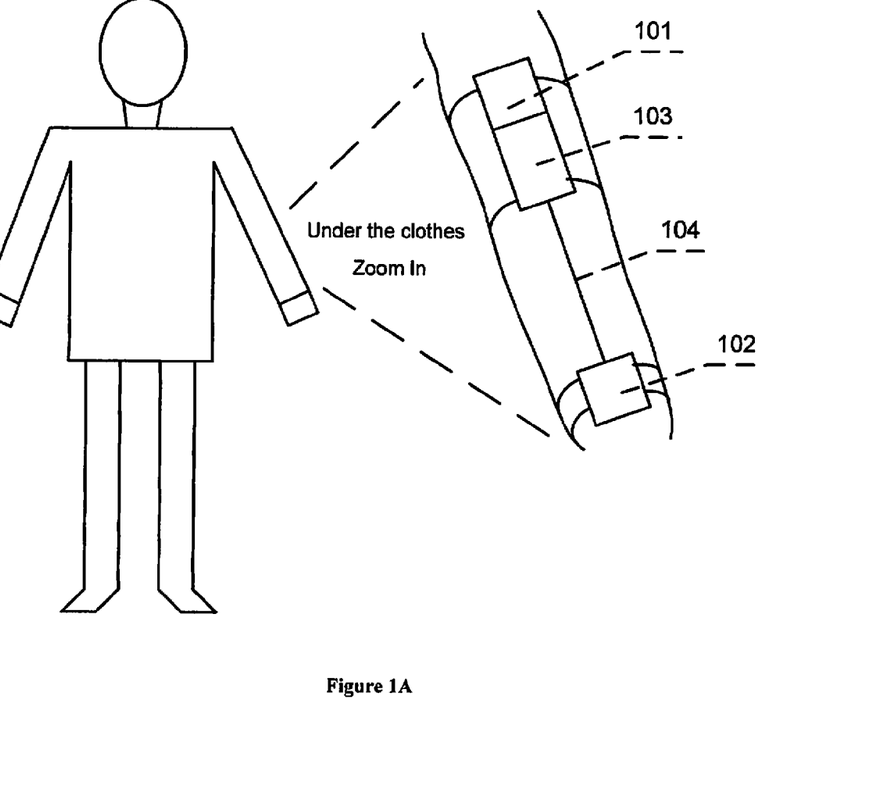
FIG. 1A shows a potential patient wears the device of this invention on an arm.

FIG. 1A shows a high risk person wearing the device on his arm. A zoomed illustration of the device is shown on the right side. The device includes a first sensor unit 101 and a second sensor unit 102. In the illustrative diagram, the sensing unit 101 is directly attached to the processor 103 while the sensor unit 102 connects to the unit 103 via cable 104. The processor 103 processes the signals received from the sensor unit 101 and 102. The unit 103 performs the arithmetic calculations and indicates when a stroke's onset occurs. The processor 103 comprises one or more of a microprocessor, microcontroller, digital signal processor (DSP), application specific integrated circuit (ASIC), field programmable gate array (FPGA) or other programmable electronic components. The processor 103 also includes a software program to execute the intended functions. The device is worn on the arm under the clothes and would not interfere with the normal daily activities such as sit, walk, sleep, etc.

Figure 1B:
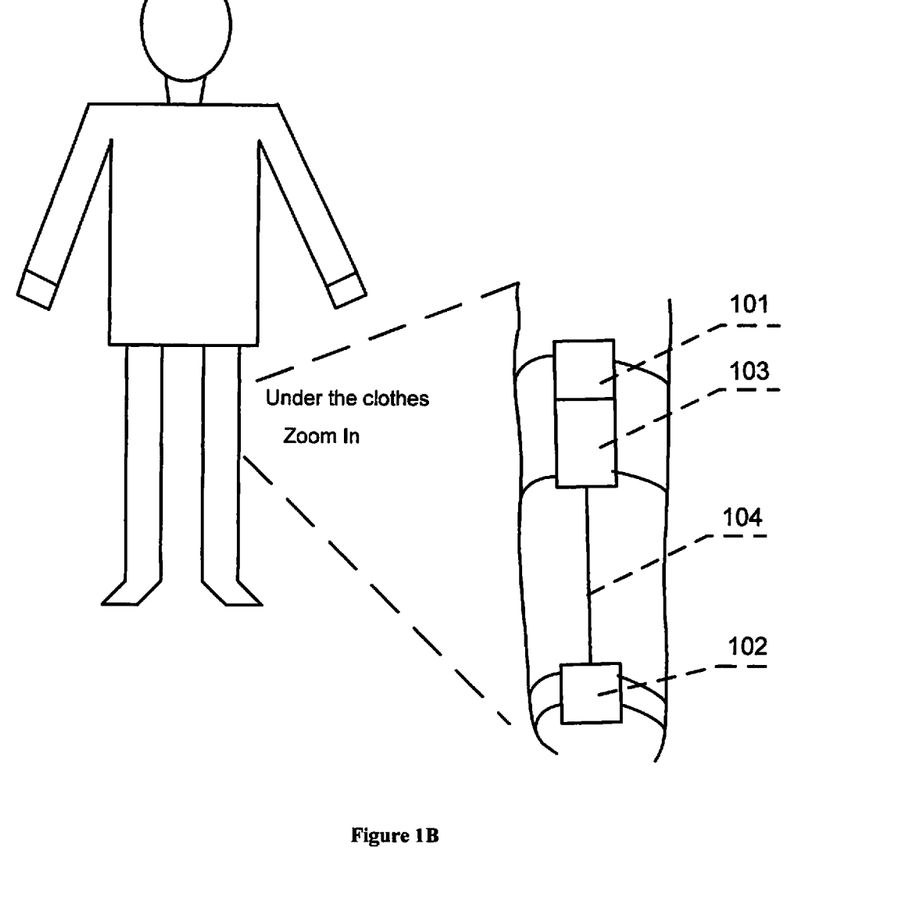
FIG. 1B shows a potential patient wears the device on a leg.

FIG. 1B shows a person wearing the device on his leg. Similar to FIG. 1A, the person who continuously wears this device can also carry out the normal regular activities without significant interferences from the device.

Figure 1C:
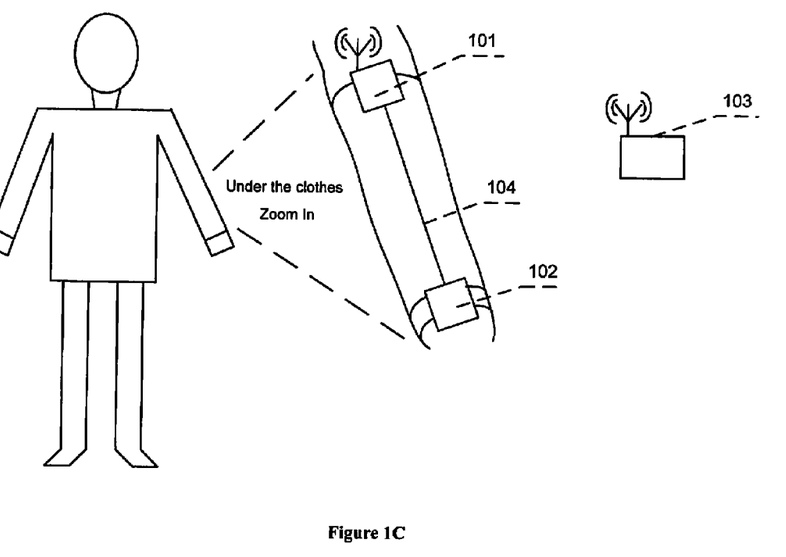
FIG. 1C shows a potential patient wears both sensor units on an arm while the processor is detached from the patient and uses wireless technologies to communicate with the sensor units.

FIG. 1C shows another method to configure the apparatus. A potential patient wears both sensor unit 101 and 102 on an arm while the processor 103 is detached from the patient and uses wireless technologies to communicate with the two sensor units. The two sensor units use 104 to communicate with each other and share one wireless connection to the processor 103.

Figure 1D:
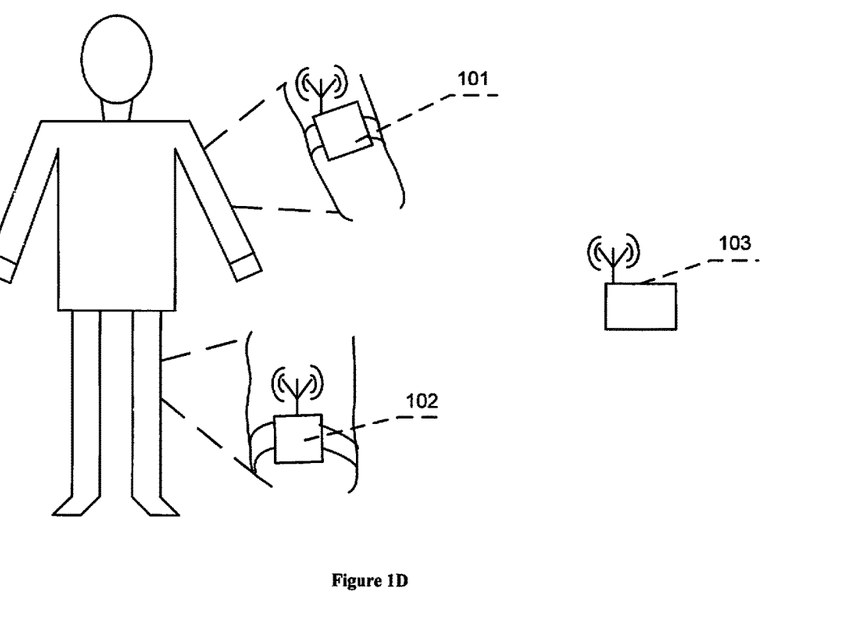
FIG. 1D shows a potential patient wears one sensor unit on an arm and the second sensor unit on a leg. Each of the sensor units has its own wireless connection to communicate with the separate processor unit.

FIG. 1D shows another method to configure the device. A potential patient wears the sensor unit 101 on an arm and the sensor unit 102 on a leg. Each of the sensor units has its own wireless connection to communicate with the separate processor 103.

Figure 2:
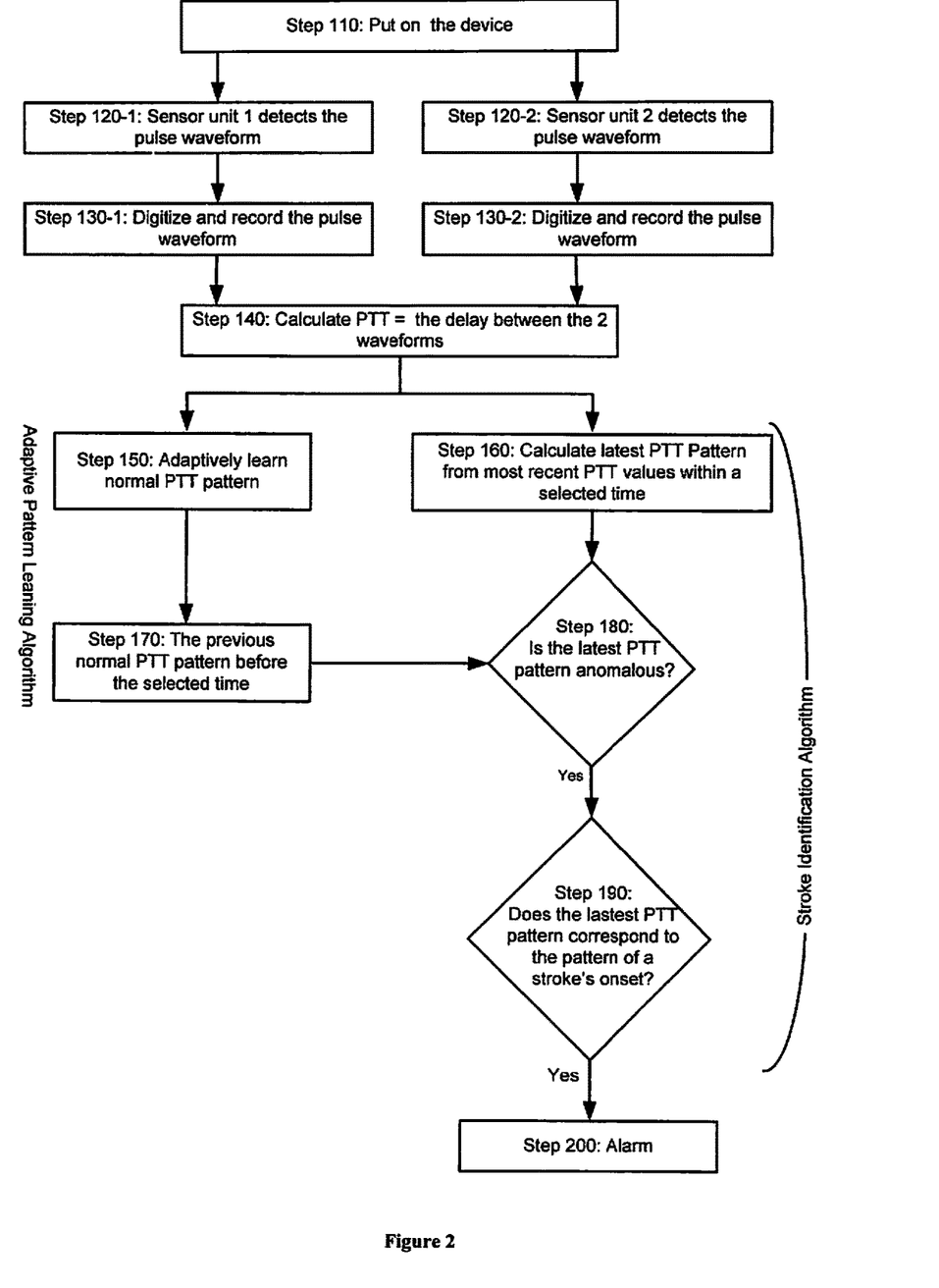
FIG. 2 is a flow chart for showing the processes used by the method in this patent from putting on the device to a stroke onset alarm.

FIG. 2 is a flow chart showing an embodiment about the processes carried out by this invention. The processes start with wearing the apparatus (step 110). The two sensor units continuously measure the arterial pulse wave respectively on two separate arterial sites on a human body (steps 120-1 and 120-2). The output of each sensor unit is an analog electrical signal. An analog to digital (ADC) is used to convert the analog sensor output into digital format so that an arterial pulse waveform is represented by a series of digital data (steps 130-1 and 130-2). By comparing the two series of digital data from the two separate sites, the pulse transit delay time (PTT) between the two waveforms is calculated (step 140). The pattern learning algorithm monitors the change of PTT and learns the normal PTT patterns for the patient (step 150). The stroke identification algorithm calculates the latest PTT pattern from the most recent PTT values within a selected time (step 160). The latest PTT pattern is then compared to the normal PTT pattern (step 180), which was obtained with the previous PTT values before the selected time (step 170). If the latest PTT pattern from the selected time is anomalous (step 180) and corresponds to the pattern of a stroke's onset (step 190), an alarm is sent out (step 200).

Figure 3:
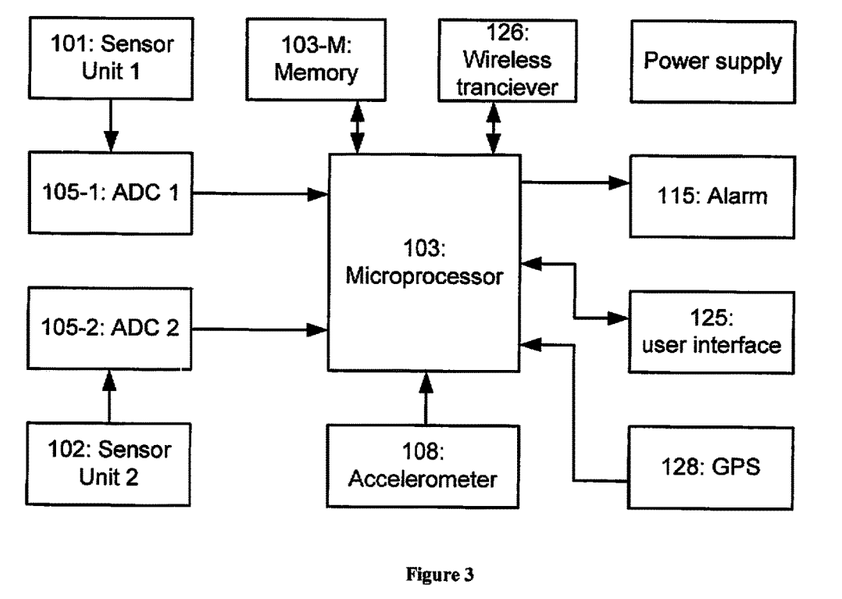
FIG. 3 describes a block diagram and major components in the apparatus.

FIG. 3 is a functional block diagram showing another embodiment about the major components in the apparatus. The stroke onset monitoring and alarm apparatus includes the first and second sensor units 101 and 102 to continuously detect the pulse wave and transmit the analog signals to the first and second analog to digital converters (ADC) 105-1 and 105-2 which respectively convert the analog signals to digital electrical signals. The ADC 105-1 and 105-2 then transmit the digital signals to the processor 103 that uses memory 103-M to temporarily store the digital signals. The processor 103 performs calculations and control functions. The processor 103 also executes calculations to analyze movement effects by receiving and applying signals from an accelerometer 108. The accelerometer 108 detects the patient's movement and position. The memory 103-M is used for data storage. The alarm unit 115 is implemented to send audio signals to nearby caregivers. The wireless transceiver 126 sends wireless indication to remote caregivers or medical team assigned to monitoring the patient. The wireless message includes a summary of the patient's information, alarm and location. The global position system (GPS) 128 measures the patient's location. The apparatus further includes a user interface 125 to show the operational condition of the apparatus and measurement results. The user interface 125 can also be used for the device user to enter commands to control and program the apparatus. The apparatus further includes a power supply to provide power to operate the electronics. FIG. 3 only shows the major components for the purpose of understanding the invention while leaving out all the circuit details such as resistors, capacitors, inductors, amplifiers, filters, etc.

More specifically, the present invention presents a new apparatus and method using PTT for a stroke alarm because PTT and BP are related to each other as will be further described and explained below. The sudden change of a BP pattern corresponds to a sudden but inverse change of a PTT pattern. Using PTT over the blood pressure for detecting a stroke's onset has a key advantage: The PTT measurement device is continuously wearable. Unlike oscillometry and sphygmomanometry, no cuff is needed for the PTT based method. The patient can wear the device comfortably while performing daily activities at office, home or travel. The device can also be worn during sleep.

Figure 4:
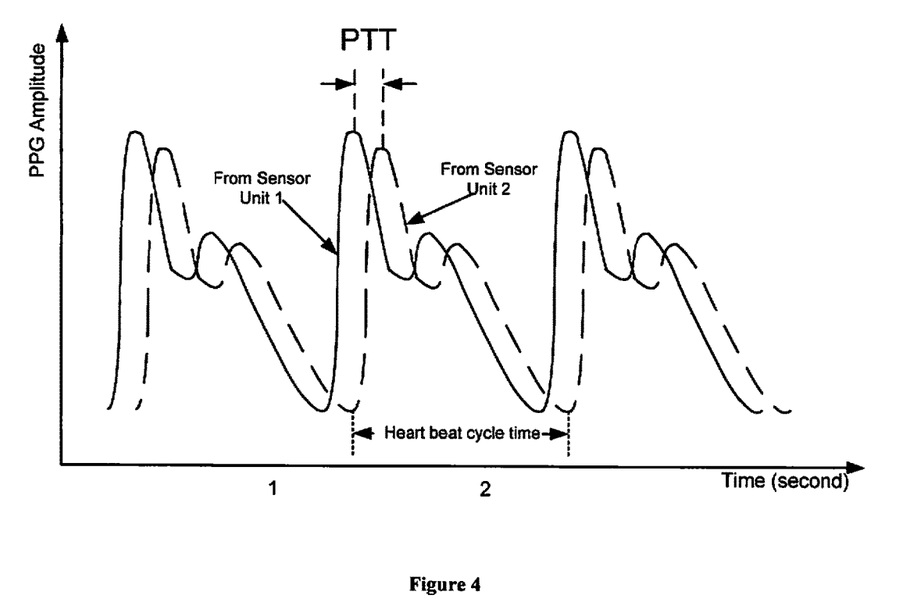
FIG. 4 is a diagram that illustrates the PPG waveform and pulse transit time (PTT) as the delay time between the PPG waveforms from two different arterial sites.

As discussed in Paragraphs [0015] to [0018], the methods of the present inventions are based on the research on the clinical data and evidences. The methods are further illustrated with descriptions of the following drawings. FIG. 4 illustrates the PPG waveforms and pulse transit time (PTT). The 2 waveforms are from the two sensor units respectively on two different arterial sites. The pulse wave sensor in each of the two sensor units is a photoplethysmography (PPG) sensor. The waveform in solid line is recorded by the sensor unit 1 on an arterial site. The waveform in dashed line is recorded by the sensor unit 2 on a separate arterial site. PTT is the time for an arterial pulse wave to transit from one site to another site on human arterial tree. In the figure, PTT is shown as the delay time between the two PPG waveforms from two different arterial sites. Similar to blood pressure, PTT is a blood circulation characteristic hemodynamic parameter. PTT is typically in the order of milliseconds. The cycle time for a PPG waveform at a fixed arterial site is the heart beat cycle time, which is around a second.

PTT is the time difference between the corresponding points in the two waveforms recorded from the two arterial sites. The measuring points can be peak, foot, peak of $1^{st}$ derivative of the waveform, peak of $2^{nd}$ derivative of the waveform, or other corresponding points on the waveforms. PTT and blood pressure are inversely related to each other. Specifically, PTT and BP can be calculated from each other according to the following equation (Nichols, et al., McDonald's Blood Flow in Arteries, Theoretical, experimental, and clinical principals. $4^{th}$ ed., Hodder Arnold Publication, London, 1998, ch. 3):

$$PWV = \sqrt{\frac{T*E0*e^{a*BP}}{\rho*d}} \quad \text{(Equation 1)}$$

$$PTT = \frac{\text{Distance}}{PMV} \quad \text{(Equation 2)}$$

In the above equations, PMV is the pulse wave velocity. BP is the blood pressure. Distance is the physical distance between the 2 sensor sites. Coefficient T is the blood vessel wall thickness; $\rho$ is the blood density; d is the interior diameter of the vessel; E0 is the arterial wall elasticity; a is a constant. The coefficients are physically characteristics of a person's cardiovascular system. They are stable for a person for a period, but gradually change as the person ages. Specifically, several researchers have tried to develop a new BP meter based on PTT (U.S. Pat. Nos. 5,857,975; 5,649,543; 5,316,008 etc). The main challenge for the approach is inconsistency of the coefficients in Equation 1. Although the coefficients are stable for a single person for a period in his or her life, the coefficients vary from one individual to another individual. They are also different from one age to another age for the same individual. For these reasons, the researchers have not been able to produce a reliable BP meter, which can give a BP value close to that measured by other BP technologies such as sphygmomanometer and oscillometry. The methods of this invention directly using PTT for stroke detection resolve the difficulties encountered when trying to calculate BP from PTT. It is also worth noting that BP is clinically used as a vital sign signal to monitor a person's health but the PMV or PTT is not. BP has standard ranges indicating hypotension, hypertension or normal. No common or standard ranges of PMV or PTT are available to indicate a person's health for all people.

Figure 5A:
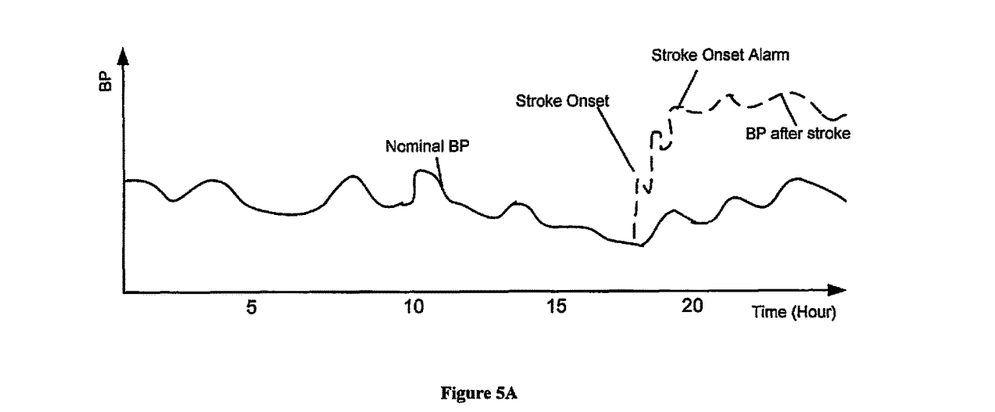
FIG. 5A is a diagram that illustrates blood pressure waveforms during normal time and when a stroke occurs.

FIG. 5A illustrates blood pressure waveforms during normal time and when a stroke occurs. The solid line is the normal blood pressure waveform. The dashed line shows the blood pressure pattern after a stroke's onset. According to a large amount of research and clinical data (Paragraph [0015-0018]), the blood pressure (BP) is changed significantly from the normal solid pattern to the dashed pattern when a stroke starts. The change of the blood pressure is due to compensatory auto-regulation mechanism to a stroke attack by a human body. This is a natural protective response to reduce further neuronal damage. The alarm occurs ~1 hour after the stroke's onset, which is well within the famous 3 hour window for the thrombolytic therapy. The BP waveforms in the diagram are shown for 24 hours. The algorithms implemented on the processor unit 103 further allow complex pattern learning and recognition analysis for better accuracy and coverage.

Figure 5B:
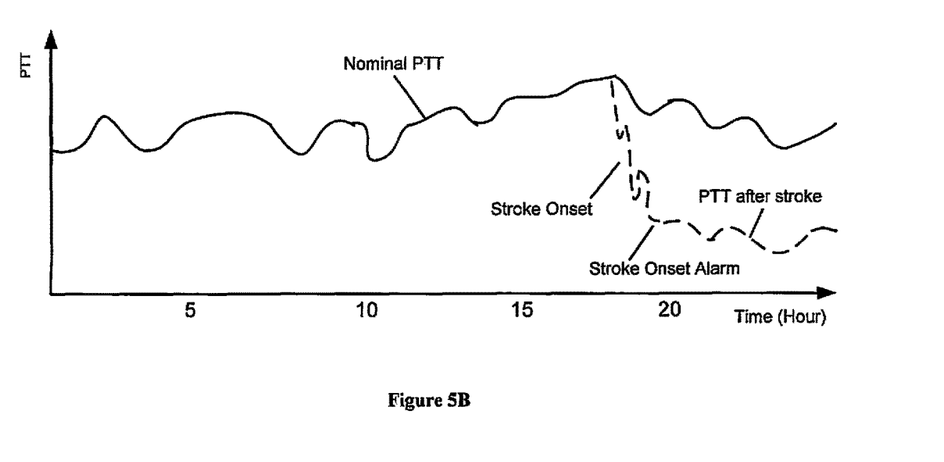
FIG. 5B is a diagram that illustrates PTT waveforms during normal time and when a stroke occurs.

FIG. 5B illustrates PTT waveforms during normal time and when a stoke occurs. PTT and BP are inversely related to each other and can be calculated from each other by Equations 1 and 2 as discussed above in Paragraph [0047]. When a stroke starts, the PTT is correspondingly changed from a normal pattern to a new pattern. The solid line is the normal PTT waveform. The dashed line shows the PTT pattern after a stroke attack. The apparatus in the patent can calculate and indicate the time when a stroke starts. The alarm occurs ~1 hour after the stroke's onset, which is well within the famous 3 hour window for the thrombolytic therapy. The processor unit 103 further runs complex pattern learning and recognition analysis for stroke identification. While theoretically both BP and PTT can be used to indicate a stroke attack, measuring and monitoring PTT are much simpler. The PTT waveforms in the diagram are shown for 24 hours.

Figure 6:
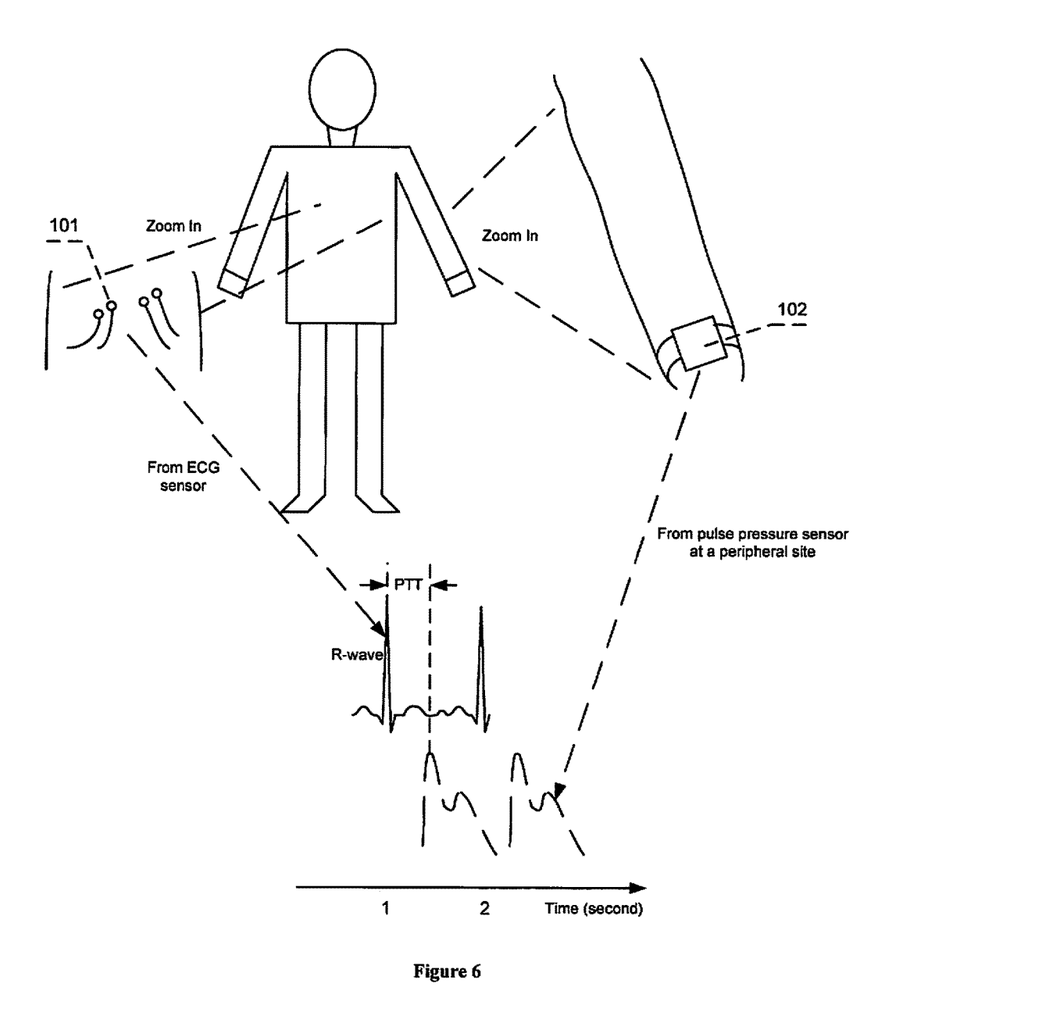
FIG. 6 shows PTT can also be the delay time between Electrocardiography (ECG) waveform and a PPG waveform from an arterial site.

FIG. 6 shows another form of PTT. An arterial pulse wave originates from the heart and travels to peripheral sites along arterial vessels. The starting point of an arterial pulse wave propagation corresponds to ECG R-wave. In the case, the sensor unit 101 is the ECG electrodes. The PPG sensor inside the sensor unit 102 measures the arterial pulse wave at a peripheral arterial site. Then the PTT is the delay time between the ECG waveform and PPG waveform from an arterial site. The measuring points are shown to be peak to peak in the figure. Other corresponding points similar to those described in can be used as well.

In another embodiment of the invention, Adaptive Normal PTT Pattern Learning Algorithm is provided: The present invention includes adaptive normal PTT pattern learning algorithm covering dynamics of normal PTT changes for a person. Similar to BP, normal PTT varies (See solid line on FIG. 5B). Each person has his or her own unique characteristic PTT pattern. After a patient starts to wear the device, the algorithm finds, calculates and memorizes the characteristics of the patient's normal PTT pattern. The PTT pattern is mathematically modeled by statistic analysis, classification and artificial intelligence. The algorithm runs continuously so that the characteristics of the normal PTT pattern are adaptively updated with the recent values when the patient's health, age or living style changes.

The pattern learning procedure starts with periodically acquiring PTT value and saving the data into memory along with corresponding real clock time and then calculates the characteristic parameters of the normal PTT pattern. The characteristic parameters include, but not limit to, average, maxim and minimum PTT values, probability distribution of the PTT values, rising, falling time and slope when the PTT changes, real time duration for each value or class, real time curve of the PTT changes, standard deviation, frequency domain spectrum, wavelet analysis, PTT change due to body position and movement as detected by accelerometers as detailed [0056]. Table 1 gives more explanations for the parameters.

TABLE 1

| PTT pattern parameter | Description |
| --- | --- |
| Average PTT value | Average of PTT values for a chosen time |
| Maximum PTT value | Maximum PTT value for a chosen time |
| Minimum PTT value | Manimum PTT value for a chosen time |
| Probability distribution of the PTT values | A plot showing the probability of all PTT values |
| Rising time | Length of time it takes PTT to rise |
| Falling time | Length of time it takes PTT to fall |
| Slope | Upward or downward slant of a PTT change |
| Real time duration | Length of time when PTT stays at a value or range |
| Real time curve | A plot showing the PTT value vs time |
| Standard deviation | Standard deviation of a value or range |
| Frequncy domain pattern | Amplitude and phase distribution vs frequency after Fourier transform |
| Wavelet analysis | Wavelet analysis on a set of PTT data |
| PTT pattern due to movement and position | PTT values when a person moves or changes position |

In another embodiment of the invention, Stroke Identification Algorithm is provided to identify a stroke's onset: The invention further includes stroke identification algorithm to decide whether and when a stroke's onset has happened. The identification algorithm calculates the latest PTT pattern from the most recent PTT data that are measured and recorded within a selected time (step 160, FIG. 2). The latest PTT pattern is then compared with the normal PTT pattern, which was calculated from the PTT data before the selected time, to decide whether the latest PTT pattern is anomalous from the normal PTT pattern. If the latest PTT pattern is anomalous and the latest PTT pattern is further determined to be corresponding to a special PTT pattern of a stroke's onset, an alarm will be triggered. The algorithm uses pattern recognition and pattern similarity analysis between the latest PTT pattern and the special PTT pattern indicating a stroke's onset to identify and detect a stroke's onset. The special PTT pattern indicating a stroke attack is determined from the patient's medical history, normal PTT pattern and clinical research data like those described in Paragraph [0015-0018]. The algorithm is implemented as a software program residing on the processor 103. For an illustrative example, when two characteristic pattern parameters including PTT value and real time duration are used, if only one of the two parameters changes beyond its normal range but the other parameter stays within its normal range, no alarm will be generated. However, if a PTT falling edge are detected and the changes correspond to a significant blood pressure elevation and, furthermore, the PTT stays at the decreased level for more than an hour, then the latest PTT pattern from the falling edge to long stay at the decreased level is considered to be corresponding to the pattern of a stroke's onset as described in Paragraph [0015-0018], FIGS. 5A and 5B. An alarm will be generated along with the time indication about when the decrease of the PTT value starts. The time indication is important for prescribing a drug like tPA. In implementation, more complex pattern learning and stroke identification algorithms can be used for detecting a stroke's onset more accurately. Mathematically, the stroke identification algorithm uses pattern recognition and pattern similarity analysis between the latest PTT pattern and the special PTT pattern to identify and detect a stroke's onset. The algorithm also calculates and indicates the confidence level or probability of detecting a stroke attack.

In addition to calculate PTT, the measurements and data from the 2 sensor units can also be directly used for detecting an abnormal health condition. Specifically the arterial pulse wave data is available in the method, the arterial pulse wave from a single arterial site can be used to analyze the change and enhance the stroke onset detection. For example, the amplitude of the arterial pulse waveform can be easily obtained. When the sudden PTT pattern change is accompanied by the amplitude change of the arterial pulse waveform, the stroke detection is further confirmed.

The processor 103 is implemented with software programs to carry out the tasks of sensor data acquisition, calculation and communication continuously or periodically. The time interval between the PTT acquisitions is programmable. For example, a new set of PTT data is acquired and processed every 5 minutes. The software programs also perform initial estimation for the characteristic parameters if the device is worn $1^{st}$ time by a patient.

In another embodiment of the invention, Motion Sensor Is Used to Improve Alarm Accuracy: The present invention further includes an accelerometer or inclinometer to monitor the patient's movement, exercise, position and gesture. Similar to BP, PTT will change more when the patient does strenuous exercises. The adaptive normal pattern learning algorithm finds the normal relationship between the movement and PTT. Based on the data from the accelerometer or inclinometer, the pattern learning algorithm recognizes the PTT pattern during the movements. The stroke identification algorithm filters out the PTT changes due to the patient's physical activities when deciding a stroke indication. This method helps minimize the possibility of unnecessary alarms and improve the accuracy of a stroke onset indication. In addition, the accelerometer or inclinometer detects the orientation of the multiple sensor units and make compensation to PTT due to hydrostatic effect when a patient changes his or her position such as standing up or lying down. Multiple motion sensors can be further used to sense the position and movement of different body parts and arterial pulse wave sensor units.

In another embodiment, the arterial pulse wave sensor for the pressure wave data acquisition and PTT measurement comprises photoplethysmography (PPG) sensor, which is widely used in oximeter on market for many years. The PPG sensor uses light-emitting diode (LED) to transmit light to skin, and a photodiode to detect the received light after passing the tissue. It can be used to detect blood volume changes in a blood vessel (Challoner et al., "Photoelectric plethysmography for estimating cutaneous blood flow Non-Invasive Physiological Measurements", vol 1 ed P Rolfe, London: Academic, pp 125-51, (1979)). The delay time between the PPG waveforms from two different arterial sites on a human body is detected by using sensor 101 and 102 of this invention to measure the pulse transit time (PTT). The PPG sensor does not involve a cuff, which introduces uncomfortableness during a continuous wearing. Alternatively, a piezoelectric or other ultrasound transducer, laser Doppler or other optical blood flow sensor, pressure or force sensor, or any other sensor that can sense the arterial pulse wave and convert it to an electrical signal for acquiring data to calculate PTT can be used. As shown in FIG. 6, PTT can also be measured from electrocardiography (ECG) to a peripheral site. In this case, additional ECG electrodes can be used to provide ECG R-waveform.

In another embodiment, an array of the pulse wave sensors is used inside a sensor unit to help align with an arterial site when a patient wears the device. The sensor unit may include one or multiple sensors. When an array is used, the sensor unit covers greater area and is more likely to cover an arterial site. After the device is worn, the software program in the processor 103 automatically measures the signal strength from each sensor and finds the most sensitive sensor in the sensor array and uses the waveform from that sensor for PTT calculation.

In another embodiment, the sensor unit comprises one or more kinds of pulse wave sensors. The combination of the different sensors provides a compensation of different sensor technologies. They can also calibrate each other. For example, the sensor unit includes both PPG sensor and ultrasound transducer. The PPG sensor is low cost and easy to implement but more sensitive to skin color. The ultrasound transducer is more costly to implement but less sensitive to skin color. Using the 2 sensors inside a sensor unit makes the design more robust for different arterial sites or patients.

In another embodiment, the arterial site for the PTT measurement can be on hand, arm, neck, leg, foot, ear, head, body or any other arterial site on a human body. In the illustrative FIGS. 1A, 1B, 1C and 1D, an arm and leg are used. Depending on the sites selected, their distance and PTT will accordingly change. After the two sites are chosen, they shall be kept same for the PTT value to be comparable.

In another embodiment, the sensor data acquisition and algorithmic calculations are done locally by the device being worn on a body and the result alarm is sent out audibly and wirelessly to both nearby and remote care team. Alternatively, the sensor units send the digitalized waveform data to a separate processor unit via a wireless technology such as Bluetooth, Zigbee, Wi-Fi etc (FIGS. 1C and 1D). The processor unit 103 is not physically attached to the worn sensor units. The wireless transceiver can sit on one sensor unit which also collects the data from the other sensor unit (FIG. 1C). Optionally, both sensor units include the wireless capability to independently exchange data with the processor unit 103 (FIG. 1D).

In another embodiment, extra connections 104 between the two sensor units 101 and 102 are included to provide communications between the 2 sensor units.

In another embodiment, in addition to use BP and PTT for detecting a stroke's onset as described above, it is understood that the normal pattern learning algorithm and the stroke identification algorithm in the present patent can be applied to other related hemodynamic parameters. The hemodynamic parameters may be measured by the method using 2 pulse wave sensor units on 2 different arterial sites as described in this patent or may be measured by another technology. Specifically, as described in Paragraph these methods and algorithms may be applied to BP when current BP technology or a new emerging BP measurement technology is improved to be continuously wearable. The applications of using BP data for stroke onset detection according to the disclosures made in this invention are within the scopes of the present patent. It is further understood that the inventions disclosed in this patent further include use of pulse wave velocity (PWV), blood pressure, mean arterial pressure (MAP), blood flow speed, cardiac output or other related hemodynamic parameters since the parameters can be deduced from each other. For example, PMV is equal to Distance/PTT. For the $2^{nd}$ example, MAP is equal to (systolic blood pressure+2*diastolic blood pressure)/3. For the $3^{rd}$ example, cardiac output is equal to mean blood pressure divided by systemic vascular resistance. For the $4^{th}$ example, according to simplified Bernoulli equation, blood pressure and blood flow speed can be related as:

$$\Delta P = \frac{\rho}{2} \Delta V^2 \qquad \text{(Equation 3)}$$

$P$ is blood pressure, $V$ is blood flow speed, $\rho$ is blood density

In another embodiment, the method and apparatus in this patent are used as the first alert of a stroke's onset. The above PTT-based result is combined with other biochemical assays to further confirm the detection. After the first alarm by the PTT-based method, the patient or caregiver takes biological examples such as blood samples from the patient, and performs biochemical analysis to look for stroke biomarker, and then decide whether to go to a hospital. If a chemical or biochemical sensor has very high sensitivity, it can also be included in the pulse wave sensor unit to detect a stroke biomarker from the skin of the patient's body. The stroke onset indication can also be used to make a decision for immediate drug delivery.

During clinical practice, the medical professional can choose to prescribe the apparatus to a certain group of high risk stroke patients depending on the patient's stroke history and subtype of the stroke, blood pressure history, family disease history, overall health, other diseases etc. The software program implemented in the processor 103 further allows the options such that the apparatus can be flexibly programmed and adjusted differently for different groups of potential stroke patients. For example, the threshold may be set to a lower value for those patients with prior stroke history and with elevated blood pressure when the previous stroke occurred for better protection of this type of patients.

In some cases without real stroke onset, PTT can go to be close to alarm level. This includes alcohol and some drugs etc. The use of these drugs or alcohol belongs to artificial manipulation of PTT level. Therefore, it is understood that false alarm may occur when a person uses the apparatus for monitoring a stroke but takes special drug or alcohol. The apparatus in this patent further includes a switch or button allowing a patient to turn off the stroke alarm when he needs to take this kind of drug or alcohol.

Furthermore, in another embodiment, the method of the present patent can also be applied to other diseases such as myocardial infarction, vascular aneurysm and death by learning the normal PTT pattern and detecting a sudden PTT pattern change corresponding to the disease's onset. In myocardial infarction or heart attack, a coronary artery is blocked and cannot transfer enough blood to heart muscles. Then the heart's capacity of pumping out blood into other arterial vessels becomes impaired. The dynamic of PTT will show a different pattern. In the case of death, blood pressure will drop. PTT will become longer and longer. Eventually, PTT will be infinite. Similar mechanism can be applied to vascular aneurysm. The methods in this patent can detect these kinds of cardiovascular diseases. Using pattern recognition and pattern similarity analysis to detect these disease onsets is also within the scope of the present patent application.

In another embodiment, the present apparatus is used to monitor and warn the prognosis of chronic cardiovascular diseases such a hypertension, arrhythmia, hypotension, congestive heart failure, valvular heart disease, cardiac muscle disease etc. For example, PTT and blood pressure (BP) are related to each other. If a person has hypertension and his BP goes up as a trend for several weeks or several years, the PTT will become shorter as a trend. The mean, minimum and maximum value and ranges recorded in memory 103-M will change accordingly. The software in the processor 103 then calculates the trend and notifies the patient to see a doctor. For the $2^{nd}$ example, if a person has arrhythmia, the heart beat pattern and resultant PTT pattern will be different. The software in the processor 103 detects and identifies the abnormality and gives an alarm. Furthermore, all the stored data in the electronic memory can be downloaded to a personal computer for more analysis via a common communication protocol such as Universal Serial Bus (USB).

Use Example. The following case illustrates how the device in the present patent would benefit a stroke patient. Lady X is a woman. She is 70 year old and lives with her husband. Her regular blood pressure is normal, about 115 mmHg for systolic and 70 mmHg for diastolic. She eats healthy food. The only concern she has is about a potential stroke attack since both her father and older brother died of stroke about 10 years ago. Unfortunately, her concern became true two years ago when she had a stroke attack at night. On the 2nd morning, her husband found she could not stand and he called 911. She was sent to the emergency room. After many tests including MRI, she was diagnosed to have an overnight ischemic stroke attack. Since the couple could not tell the time when the stroke's onset started, the doctor could not decide whether the onset happened within 3 hours and did not prescribe a thrombolytic medicine like tPA. After other treatments and five month physical therapy, finally she could stand and walk but with a cane. Six month ago, she had 2nd stroke attack. This time, the event occurred on a noon when the couple was having lunch. Luckily her husband noticed her change immediately. Her blood pressure pattern became abnormal. She was quickly sent to hospital. She was treated with tPA and recovered within 2 weeks this time instead of 5 months of recovery after the $1^{st}$ stroke attack. After the 2 episodes, she became very worried and did not know when the next attack would come. Her husband and children tried to monitor her consistently. They lived in constant fear of another stroke attack, especially at night. She sometimes joked that she might not wake up on a morning.

Last month, after learning the new apparatus in the present patent, she immediately decided to try the device and started to wear it on her left arm. Two weeks ago, she had a 3rd stroke attack at 3 AM. Her husband was in sleep. This time, fortunately, the device detected the stroke's onset and alerted her husband and care team. She was treated with tPA. She recovered within 5 days. The device gives her peace of mind. She wears it everyday. Now she is an advocate of the device.

Although the present invention has been described in terms of the presently preferred embodiments, it is to be understood that such disclosure is not to be interpreted as limiting. Various alterations and modifications will no doubt become apparent to those skilled in the art after reading the above disclosure. Accordingly, it is intended that the appended claims be interpreted as covering all alterations and modifications as fall within the true spirit and scope of the invention.

What is claimed is:

1. A method for monitoring a health condition of a person comprising:
    placing and fixing at least two pulse wave sensor units on at least two separate arterial sites of the person as a continuously wearable apparatus for continuously measuring arterial pulse waves on the at least two separate arterial sites of the person;
    implementing a data and signal processor with the pulse wave sensor units to collect the arterial pulse waves measured by the pulse wave sensor units at the at least two separate arterial sites of the person who wears the apparatus;
    implementing the data and signal processor to continuously compute a time difference as a pulse transit time (PTT) between the arterial pulse waves measured at the at least two separate arterial sites; and
    implementing the data and signal processor, in real time, to continuously compare pulse transit times (PTTs) to determine a post-stroke signal to immediately generate an alarm signal when a sudden decrease of the PTT is detected.

2. The method of claim 1 further comprising:
    implementing the data and signal processor to continuously collect, sample and process the arterial pulse waves measured from the at least two pulse wave sensor units to adaptively determine a normal pulse-wave peak and a normal PTT.

3. The method of claim 2 further comprising:
    implementing the data and signal processor to continuously compare the arterial pulse waves measured from the at least two pulse wave sensor units with the normal pulse wave measurement pattern to determine a post-stroke signal when a sudden decrease of a peak of one of the arterial pulse waves from the normal pulse-wave is detected.

4. The method of claim 2 wherein:
    the step of implementing the data and signal process further comprises a step of adaptively and continuously computing and updating the normal PTT.

5. The method of claim 1 wherein:
the step of placing and fixing the at least two pulse wave sensor units further comprises a step of placing and fixing at least two photoplethysmography (PPG) sensors on at least two separate arterial sites of the person.

6. The method of claim 5 wherein:
the step or placing and fixing the at least two PPG sensors further comprises a step of placing a light-emitting diode (LED) to transmit a light to a skin tissue of the person, and placing in each of the PPG sensors a photodiode to detect a received light after the light emitted from the LED passing the skin tissue of the person.

7. The method of claim 1 further comprising:
implementing a memory on the data and signal processor for storing the arterial pulse waves measured by the pulse wave sensor units and implementing the data and signal process for continuously calculating the time difference as a pulse transit time (PTT) between the at least two arterial pulse waveforms.

8. The method of claim 7 further comprising:
implementing the data and signal process for continuously comparing the PTTs from the two pulse wave sensor units with the normal PTT to determine the post-stroke signal when a sudden significant decrease of the PTT is detected.

9. The method of claim 1 wherein:
the step of placing and fixing the at least two pulse wave sensor units at the at least two separate arterial sites further comprises a step of further placing and fixing at least one of the pulse wave sensor units with an electrocardiography (ECG) electrode for measuring an ECG R-waveform.

10. The method of claim 1, further comprising:
attaching a motion sensor on the person for monitoring and measuring physical movements of the person for more accurately monitoring and determining the post-stroke signal of the person.

11. The method of claim 10 wherein:
the step of implementing and attaching a motion sensor on the person further comprises a step of implementing and attaching an accelerometer on the person.

12. The method of claim 1 further comprising:
implementing a signal transmission unit on each of the at least two pulse wave sensor units and implementing a wireless signal transmission and receiving apparatus on the data and signal processor to receive signals from the signal transmission unit on each of the pulse wave sensor units.

13. The method of claim 12 further comprising:
implementing a wireless signal transmission and receiving apparatus to receive a wireless signal from the data and signal processor for transmitting a message for reporting a location and personal information of the person when the post stroke signal is detected.

* * * * *